United States Patent
Yamabayashi et al.

(10) Patent No.: US 8,698,210 B2
(45) Date of Patent: Apr. 15, 2014

(54) SENSOR AND METHOD FOR MANUFACTURING THE SAME

(75) Inventors: Tomoaki Yamabayashi, Hokkaido (JP); Osamu Takahashi, Hokkaido (JP); Katsunori Kondo, Hokkaido (JP); Hiroaki Kikuchi, Hokkaido (JP)

(73) Assignee: Mitsumi Electric, Co., Ltd., Tokyo (JP)

( * ) Notice: Subject to any disclaimer, the term of this patent is extended or adjusted under 35 U.S.C. 154(b) by 124 days.

(21) Appl. No.: 12/990,717

(22) PCT Filed: May 13, 2009

(86) PCT No.: PCT/JP2009/002092
§ 371 (c)(1),
(2), (4) Date: Nov. 2, 2010

(87) PCT Pub. No.: WO2009/144878
PCT Pub. Date: Dec. 3, 2009

(65) Prior Publication Data
US 2011/0042673 A1 Feb. 24, 2011

(30) Foreign Application Priority Data
May 28, 2008 (JP) .................. 2008-139045

(51) Int. Cl.
*G01N 27/414* (2006.01)
(52) U.S. Cl.
USPC .............................. 257/253; 257/53; 438/49
(58) Field of Classification Search
USPC .................. 257/53, 213, 253, 775; 438/49
See application file for complete search history.

(56) References Cited

U.S. PATENT DOCUMENTS

| | | | |
|---|---|---|---|
| 5,900,128 A | 5/1999 | Gumbrecht et al. | |
| 7,843,029 B2 * | 11/2010 | Kawahito et al. | 257/461 |
| 7,932,511 B2 * | 4/2011 | Duan et al. | 257/9 |
| 2004/0026684 A1 * | 2/2004 | Empedocles | 257/14 |

(Continued)

FOREIGN PATENT DOCUMENTS

| | | |
|---|---|---|
| JP | 62-054155 A | 3/1987 |
| JP | 10-062383 A | 3/1998 |

(Continued)

OTHER PUBLICATIONS

English translation of WO2006-103872.*

(Continued)

*Primary Examiner* — John C Ingham
(74) *Attorney, Agent, or Firm* — Washida & Associates (57) ABSTRACT

Provided is a sensor having a high sensitivity and a high degree of freedom of layout by reducing constrictions of the channel shape, the reaction field area, and the position. Provided is also a method for manufacturing the sensor. The sensor (10) includes: a source electrode (15), a drain electrode, (14), and a gate electrode (13) arranged on silicon oxide film (12a, 12b); a channel (16) arranged on the silicon oxide films (12a, 12b) and electrically connected to the source electrode (15) and the drain electrode (14); and a reaction field (20) arranged on the silicon oxide films (12a, 12b). The reaction field (20) is formed at a position on the silicon oxide film (12a), the position being different from a position for the channel (16). With this configuration, it is possible to independently select the shape of the channel (16) and the area of the reaction field (20). This enables the sensor (10) to have a high measurement sensitivity and a high degree of freedom of layout.

9 Claims, 9 Drawing Sheets

(56) References Cited

U.S. PATENT DOCUMENTS

| | | |
|---|---|---|
| 2006/0052947 A1* | 3/2006 | Hu .................................. 702/20 |
| 2006/0205013 A1 | 9/2006 | Shim et al. |
| 2007/0231211 A1 | 10/2007 | Yoo et al. |
| 2007/0284630 A1 | 12/2007 | Baumann et al. |
| 2008/0286762 A1 | 11/2008 | Miyahara et al. |
| 2009/0114919 A1 | 5/2009 | Kawahito et al. |
| 2009/0153130 A1 | 6/2009 | Shim et al. |

FOREIGN PATENT DOCUMENTS

| | | |
|---|---|---|
| JP | 2001-242131 A | 9/2001 |
| JP | 2004-085392 A | 3/2004 |
| JP | 2004-108815 A | 4/2004 |
| JP | 2005-218310 A | 8/2005 |
| JP | 2005-229017 A | 8/2005 |
| JP | 2006-201178 A | 8/2006 |
| JP | 2007-139762 A | 6/2007 |
| JP | 2007-526466 T | 9/2007 |
| JP | 2007-304089 A | 11/2007 |
| TW | 200723530 | 6/2007 |
| WO | 2006/103872 A | 10/2006 |
| WO | 2007/119626 A1 | 10/2007 |

OTHER PUBLICATIONS

Notice of Reasons for Rejection for Japanese Patent Application 2008-095237, Japanese Patent Office, May 22, 2012.

* cited by examiner

SENSOR AND METHOD FOR MANUFACTURING THE SAME

TECHNICAL FIELD

The present invention relates to a sensor such as biosensor, pH sensor, or the like; and a manufacturing method thereof. More particularly, the present invention relates to a sensor provided with a field effect transistor (FET), and a manufacturing method thereof.

BACKGROUND ART

Heretofore, sensors such as biosensors and pH sensors with an FET have been proposed (see Patent Literatures 1 to 3). Generally, with a sensor that utilizes an FET, a source electrode and a drain electrode are electrically via a channel formed on an insulating film. A reaction field for a detection target substance is formed on the channel. A reaction membrane for immobilizing a detection target substance is provided on the reaction field. Then, normally, a gate voltage is applied by means of a gate electrode arranged on the reaction membrane, and then the concentration or the like of a detection target substance provided in the reaction field is measured by detecting a source-drain current at that time.

CITATION LIST

Patent Literature

[PTL 1] Japanese Patent Application Laid-Open No. 2004-85392
[PTL 2] Japanese Patent Application Laid-Open No. 2006-201178
[PTL 3] Japanese Patent Application Laid-Open No. 2007-139762

SUMMARY OF INVENTION

Technical Problem

In an above-described sensor, the channel functions as a sensing section. The amount of change of a source-drain current with respect to a gate voltage (that is, measurement sensitivity) differs depending on the shape of the channel. It is thus desirable for the shape of the channel to be able to be selected arbitrary according to the kind and so forth of a detection target substance to be measured.

Meanwhile, the area of the reaction field also affects a potential applied to the FET substrate via a detection target substance. Therefore, measurement sensitivity also differs depending on the area of the reaction field. It is thus desirable for the area of the reaction field to be able to be selected arbitrary according to the kind and so forth of a detection target substance to be measured. Furthermore, a broad range selection of the location of the reaction field is desirable in view of user convenience, layout as the sensor, and so forth.

The present invention provides a sensor having high measurement sensitivity and having a high degree of freedom of layout, by reducing restrictions on the shape of the channel and on the area and position of the reaction field. The present invention also provides a manufacturing method thereof.

Solution to Problem

A first aspect of the present invention relates to a sensor that is provided with: a silicon substrate having a silicon oxide film; a source electrode, a drain electrode and a gate electrode arranged on the silicon oxide film; a channel of poly-silicon or amorphous silicon that is arranged on the silicon oxide film and is electrically connected to the source electrode and the drain electrode; and a reaction field located on the silicon oxide film.

A second aspect of the present invention relates to a method for manufacturing a sensor that includes an FET having a semiconductor substrate, a silicon oxide film formed on the surface of the semiconductor substrate, and an electrode arranged on the silicon oxide film, part of the silicon oxide film being a reaction field for a detection target substance; this manufacturing method including the steps of: forming a silicon oxide film on a silicon substrate; forming a poly-silicon film or amorphous silicon film on the silicon oxide film; doping the poly-silicon film or amorphous silicon film with an impurity; forming a source electrode and a drain electrode on the poly-silicon film or amorphous silicon film doped with the impurity; forming a gate electrode on the silicon oxide film; and forming a reaction field on the silicon oxide film.

Advantageous Effects of Invention

According to the present invention, a reaction field is located on a different position of the silicon oxide film from a position on which a channel is arranged. And therefore restrictions on the shape of the channel and on the area and position of the reaction field are reduced. And also, a measurement sensitivity of the sensor and latitude of layout of the sensor can be increased. Moreover, since the channel is formed of poly-silicon or amorphous silicon, the silicon oxide film, the drain electrode, the source electrode and the channel can be formed easily through the same kind of semiconductor manufacturing process as used for TFT manufacture. And also, the width of the channel and the thickness of the silicon oxide film can be selected easily. As a result, the measurement sensitivity of the sensor can be changed easily.

DESCRIPTION OF EMBODIMENTS

Embodiments of the present invention will be described in detail with reference to the accompanying drawings.

Embodiment 1

Sensor Configuration

Figure 1:
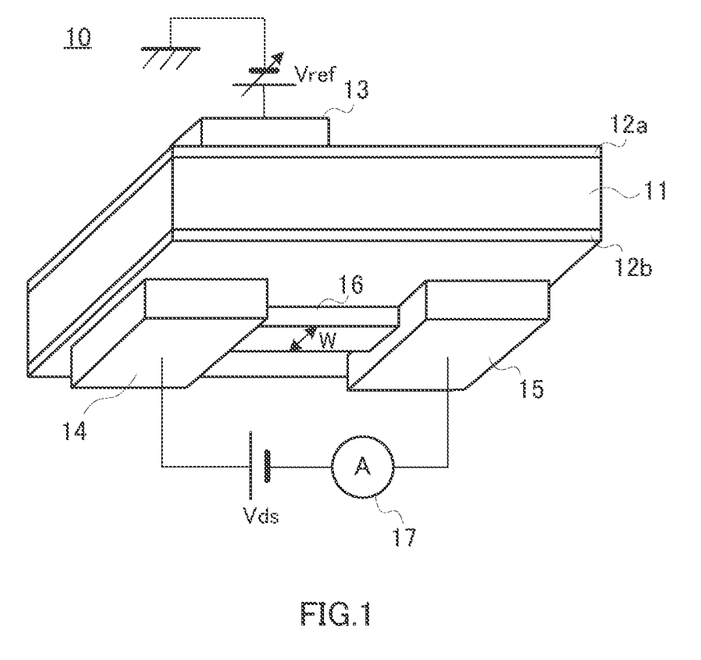
FIG. 1 is a perspective view schematically showing the configuration of a sensor according to Embodiment 1 of the present invention.
Figure 2:
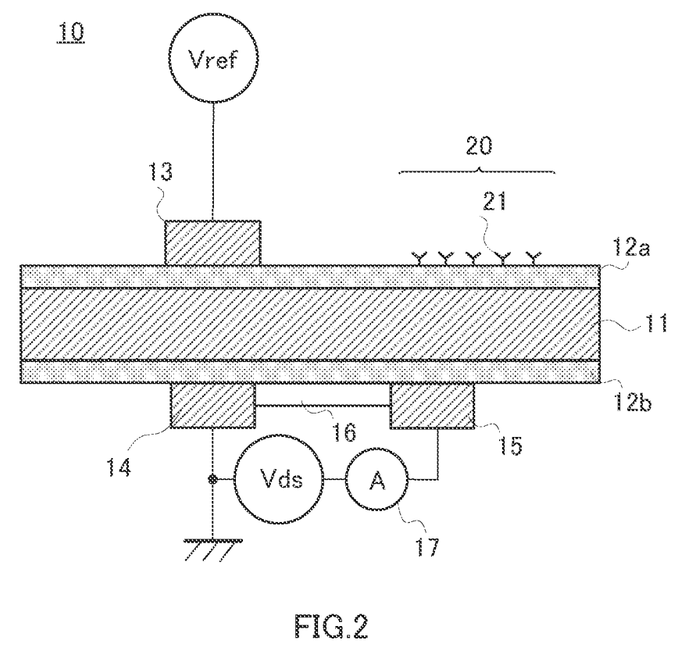
FIG. 2 is a cross-sectional view schematically showing the configuration of a sensor according to above Embodiment 1.

FIG. 1 is a perspective view schematically showing the configuration of a sensor according to Embodiment 1 of the present invention. FIG. 2 is a cross-sectional view schematically showing the configuration of the above sensor. This embodiment is an example in which a sensor of the present invention is applied to a biosensor, pH sensor, or the like.

As shown in FIG. 1 and FIG. 2, sensor 10 has silicon oxide films 12a and 12b, which function as insulating films, formed on both surfaces of silicon substrate 11.

Gate electrode 13 is arranged on the surface of the silicon oxide film 12a. Reference voltage Vref is applied by gate electrode 13. Gate electrode 13, silicon oxide film 12a and silicon substrate 11 configure a metal-insulator-semiconductor (MIS) structure. Therefore, a gate voltage is not applied directly to silicon substrate 11. The material of gate electrode 13 is not particularly limited, as long as it is electrically conductive, and may be a metal such as gold, platinum, titanium and aluminum, or a conductive resin.

On the other hand, drain electrode 14 and source electrode 15 are arranged on the surface of the silicon oxide film 12b. Drain electrode 14 and source electrode 15 are electrically connected via channel 16 on silicon oxide film 12b.

In the case of this embodiment, channel 16 is formed of poly-silicon. As a result, silicon oxide film 12b, drain electrode 14, source electrode 15 and channel 16 configure a typical thin film transistor (TFT) structure. And therefore silicon oxide film 12b, drain electrode 14, source electrode 15 and channel 16 can be formed easily with the same kind of semiconductor manufacturing process as used for TFT manufacture.

Also, since channel 16 is formed of poly-silicon, width W of channel 16 can be selected easily through a semiconductor manufacturing process compared with a case in which channel 16 is formed of carbon nano-tubes or the like.

Drain electrode 14 and source electrode 15 are connected via an external wiring including power supply Vds and ammeter 17. By this means, a predetermined voltage is applied between drain electrode 14 and source electrode 15 by power supply Vds, and a current that flows in channel 16 is measured by ammeter 17.

The distance between drain electrode 14 and source electrode 15 is not particularly limited, but is normally on the order of 0.5 to 10 [μm]. This distance may be reduced in order to facilitate connection between the each electrode via channel 16. The shape and size of the source electrode and drain electrode are not particularly limited, and can be set as appropriate for a particular purpose.

As shown in FIG. 2, reaction field 20 is located on the surface of silicon oxide film 12a. Reaction field 20 means an area in which a sample solution to be measured is provided.

It is preferable that reaction field 20 and gate electrode 13 are arranged on one of the silicon oxide films 12a and 12b (in FIG. 2, arranged on silicon oxide film 12a). Also, it is preferable that reaction field 20 and gate electrode 13 on the silicon oxide film 12a are located close to each other as possible. For example, gate electrode 13 may be located above or around reaction field 20. In this way, a change of voltage through channel 16 in response to a concentration change of a detection target substance provided in reaction field 20 can be made larger, so that measurement sensitivity of the sensor can be increased.

It is preferable that the thickness of silicon oxide film 12a of an area in which reaction field 20 is located is less than the thickness of silicon oxide film 12a around reaction field 20. That is to say, it is preferable for reaction field 20 to be located in a concave section. By this means, not only a sample solution to be provided can be held efficiently in reaction field 20, but a line of electric force from gate electrode 13 can also be made to pass through reaction field 20 more efficiently without leaking out of reaction field 20. Alternatively, it is preferable that a barrier member surrounding reaction field 20 is provided on silicon oxide film 12a so as to efficiently hold a sample solution in reaction field 20.

When sensor 10 is used as a biosensor, molecule 21 for recognizing detection target substance should be immobilized on reaction field 20. Molecule 21 can be antibody, enzyme, lectin, suchlike protein, nucleic acid, oligosaccharide or polysaccharide, or a substance having a structure thereof. Immobilizing molecule 21 on the reaction area enables a specific protein, chemical substance, or the like to be detected specifically. On the other hand, when sensor 10 is used as a pH sensor or the like, it is not necessary to immobilize molecule 21 on reaction field 20.

Figure 3:
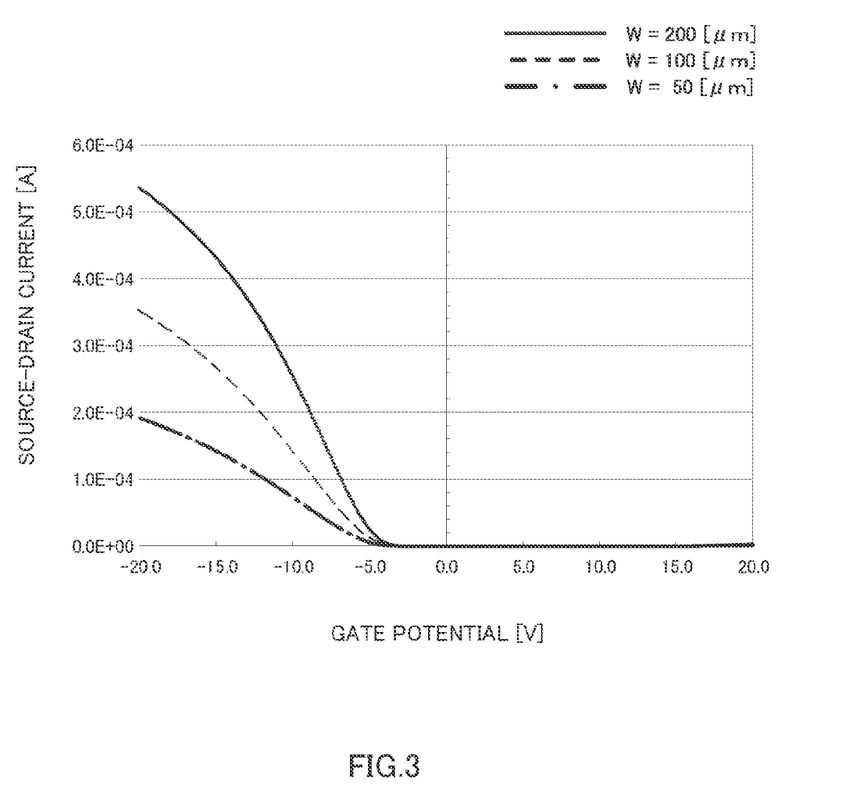
FIG. 3 shows the relationship between channel width and measurement sensitivity of a sensor according to above Embodiment 1.

FIG. 3 shows the relationship between channel width and measurement sensitivity, in which the relationship between width W of channel 16 formed of poly-silicon and source-drain current with respect to a gate voltage is shown. As can be seen from FIG. 3, the greater width W of channel 16, the greater the amount of change of a source-drain current with respect to a change of the gate voltage—that is to say, the greater width W of channel 16, the higher the measurement sensitivity of the sensor. Also, with respect to measurement sensitivity, it can be seen from FIG. 3 that width W of channel 16 is preferably on the order of 50 [μm] to 200[μm].

Figure 4:
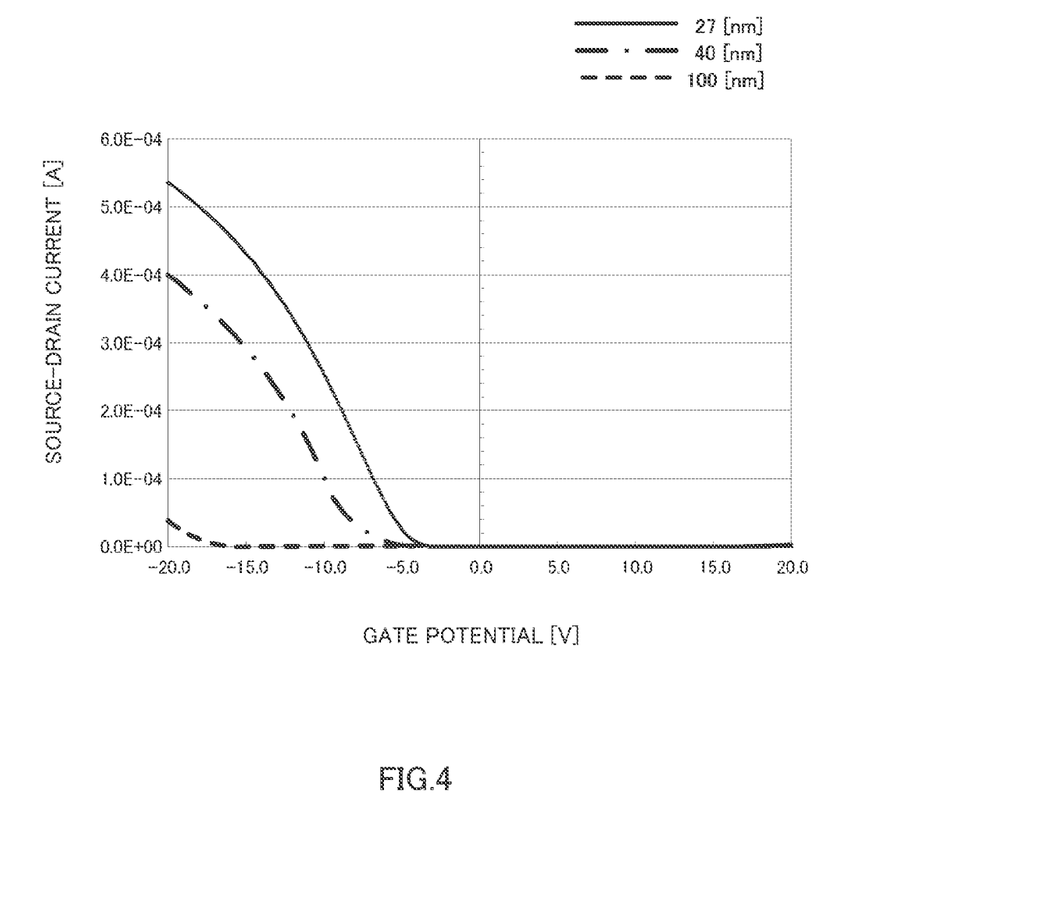
FIG. 4 shows the relationship between silicon oxide film thickness and measurement sensitivity of a sensor according to above Embodiment 1.

Furthermore, the measurement sensitivity of the sensor can be adjusted by selecting the thickness of silicon oxide film 12b through a semiconductor manufacturing process. FIG. 4 shows the relationship between the thickness of silicon oxide film 12b and the measurement sensitivity of the sensor, in which the relationship between the thickness of silicon oxide film 12b and source-drain current with respect to a gate voltage is shown. As can be seen from FIG. 4, the thinner silicon oxide film 12b, the greater the amount of change of a source-drain current with respect to a change of the gate voltage—that is to say, the thinner silicon oxide film 12b, the higher the measurement sensitivity of the sensor. Also, with respect to measurement sensitivity, it can be seen from FIG. 4 that the thickness of silicon oxide film 12b is preferably on the order of 27 [nm] to 100 [nm].

[Sensor Manufacturing Method]

The manufacturing method of sensor 10 configured as described above are explained below. FIG. 5 shows the semiconductor manufacturing process of sensor 10.

Figure 5A:
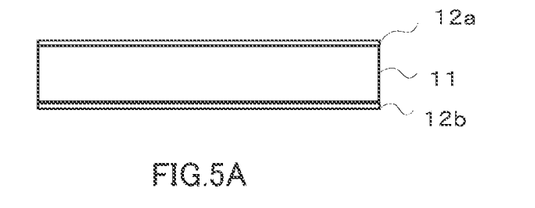
FIG. 5 shows the semiconductor manufacturing process of a sensor according to above Embodiment 1.

First, a silicon oxide ($SiO_2$) film is formed on a silicon substrate by means of thermal oxidization, as shown in FIG. 5A.

Figure 5B:
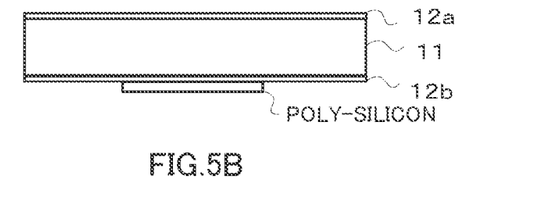

Next, a poly-silicon film is formed at a predetermined position (the position for channel 16) on the silicon oxide film, as shown in FIG. 5B. For example, amorphous silicon can first be deposited on the silicon oxide film, and then can be converted to poly-silicon by radiating with a laser beam.

Figure 5C:
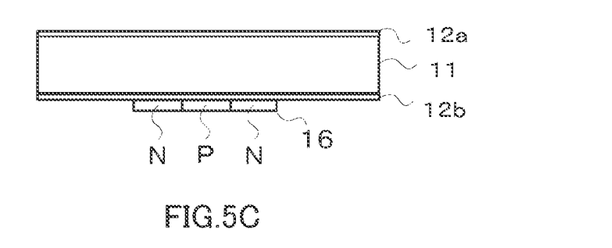

Then, NPN-type channel 16 is formed through doping the poly-silicon film with an impurity, and diffusing the impurity in the poly-silicon film by means of thermal treatment, as shown in FIG. 5C. As an example, FIG. 5C shows a case in which channel 16 is formed by making the poly-silicon film NPN-type. Channel 16 may also be formed by making the poly-silicon film PNP-type. Furthermore, channel 16 may also be formed by making the poly-silicon film NiP-type or PiP-type.

When channel 16 is NPN-type or PNP-type, the band gap of the channel is large, and therefore leakage current is smaller than in the case of an NiP-type or PiP-type channel. Consequently, NPN-type channel is preferable when the sensor has electric circuits for keeping current consumption in stand-by mode low. On the other hand, an NiN-type or PiP-type channel can be formed through one or two fewer steps than an NPN-type or PNP-type. Consequently, production cost of the sensor with NiN-type or PiP-type channel can be reduced. Consequently, an NiN-type or PiP-type channel is preferable when the sensor has electric circuit for keeping current consumption in stand-by mode moderately low. In this way, appropriate poly-silicon channel 16 is formed.

Figure 5D:
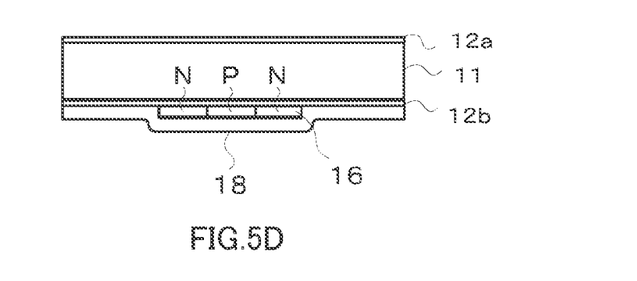

Next, inter-layer insulating film 18 covering channel 16 is formed, as shown in FIG. 5D. For the sake of simplicity, inter-layer insulating film 18 is omitted in FIG. 2.

Figure 5E:
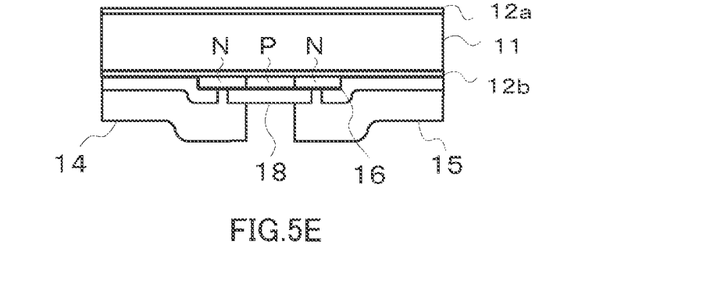

Then drain electrode 14 and source electrode 15 are formed, as shown in FIG. 5E. Drain electrode 14 and source electrode 15 are electrically connected to channel 16 via contact holes.

Next, processing (external wiring processing) for connecting drain electrode 14 with source electrode 15 via ammeter 17 is carried out, as shown in FIG. 2. Then silicon oxide film 12a and gate electrode 13 are formed, and then reaction field 20 is formed, as shown in FIG. 2.

In this way, silicon oxide film 12b, drain electrode 14, source electrode 15 and channel 16 can be formed easily with the same kind of semiconductor manufacturing process as used for TFT manufacture. Also, since gate electrode 13 and reaction field 20 are arranged at different positions from channel 16, the forming gate electrode 13 and reaction field 20 is easy, and the area of reaction field 20 can also be freely selected.

As shown in FIG. 1 and FIG. 2, silicon oxide films 12a and 12b as insulating films are formed on both surfaces of silicon substrate 11 of sensor 10.

Gate electrode 13 is arranged on silicon oxide film 12a. Reference voltage Vref is applied to gate electrode 13. Gate electrode 13, silicon oxide film 12a and silicon substrate 11 configure a metal-insulator-semiconductor (MIS) structure. Therefore, a gate voltage is not applied directly to silicon substrate 11. The material of gate electrode 13 is not particularly limited, as long as it is electrically conductive, and may be a metal such as gold, platinum, titanium and aluminum, or a conductive resin.

On the other hand, drain electrode 14 and source electrode 15 are formed on the surface of oxide film 12b. Drain electrode 14 and source electrode 15 are electrically connected via channel 16 on silicon oxide film 12b.

As described in detail above, according to this embodiment, sensor 10 is provided with source electrode 15, drain electrode 14 and gate electrode 13 arranged on silicon oxide films 12a or 12b, channel arranged on silicon oxide films 12a or 12b and electrically connected to source electrode 15 and drain electrode 14, and reaction field 20 located on silicon oxide films 12a or 12b; and wherein reaction field 20 is located at a different position on silicon oxide film 12a from a position of channel 16. This configuration allows the shape of channel 16 and the area of reaction field 20 to be selected independently. As a result, sensor 10 having high measurement sensitivity and high degree of freedom of layout can be implemented.

Also, forming channel 16 of poly-silicon enables silicon oxide film 12b, drain electrode 14, source electrode 15 and channel 16 to be formed with the same kind of semiconductor manufacturing process as used for TFT manufacture. Furthermore, width W of channel 16 can be selected with a semiconductor manufacturing process, and therefore the measurement sensitivity of sensor 10 is adjusted more easily and precisely than the measurement sensitivity of a sensor having a channel of carbon nanotubes or the like.

In this embodiment, a case has been described in which inter-layer insulating film 18 is formed, and drain electrode 14 and source electrode 15 are electrically connected to channel 16 via contact holes, as shown in FIG. 5E. But inter-layer insulating film 18 can be omitted. In such a case, drain electrode 14 and source electrode 15 electrically isolated each other can be formed directly on silicon oxide film 12b through coating the p-type region of channel 16 with resist.

Embodiment 2

Figure 6:
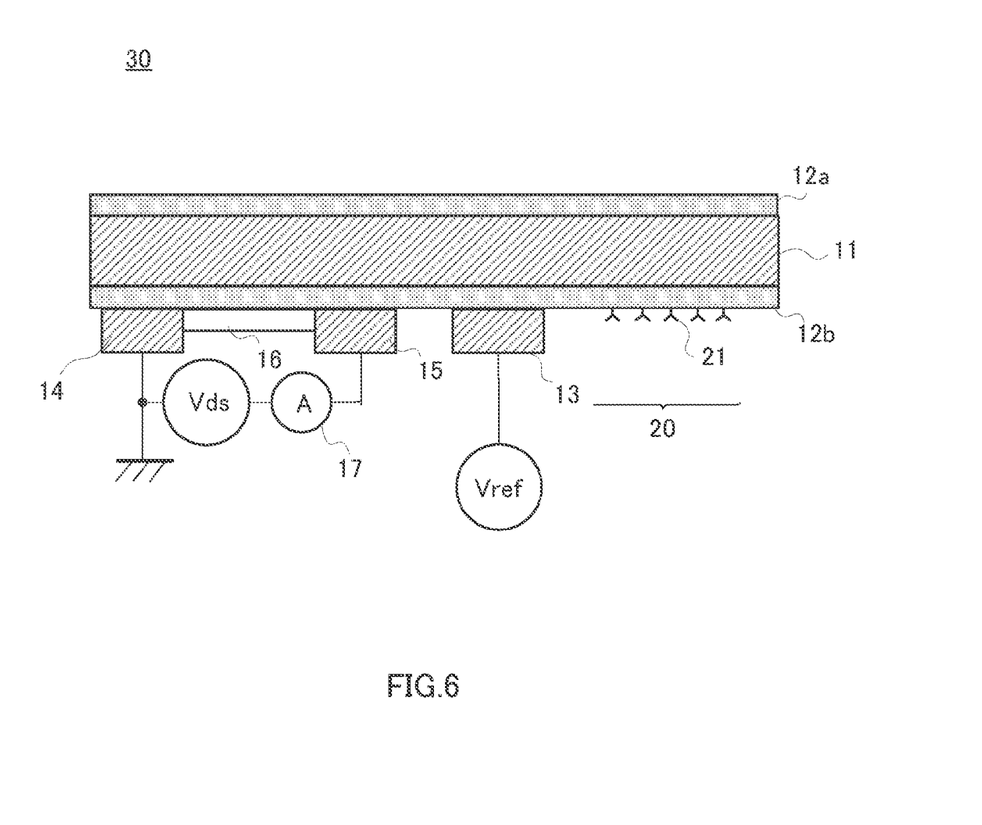
FIG. 6 is a cross-sectional view schematically showing the configuration of a sensor according to Embodiment 2 of the present invention.

FIG. 6 is a cross-sectional view schematically showing the configuration of a sensor according to Embodiment 2 of the present invention. Configuration parts identical to those in FIG. 2 are assigned the same reference codes as in FIG. 2, and duplicate descriptions thereof are omitted here.

In Embodiment 1, a case was described in which gate electrode 13 and reaction field 20 are arranged on silicon oxide film 12a which is formed on the opposite surface of the substrate with respect to silicon oxide film 12b on which drain electrode 14, source electrode 15 and channel 16 are arranged. In Embodiment 2, an example in which gate electrode 13 and drain electrode 14 are arranged on silicon oxide film 12b is described below.

As shown in FIG. 6, in sensor 30, gate electrode 13 and reaction field 20 are arranged on silicon oxide film 12b on which drain electrode 14, source electrode 15 and channel 16 are arranged. Silicon oxide film 12a of sensor 30 shown in FIG. 6 can be omitted.

As compared with the configuration shown in FIG. 6, the configuration shown in FIG. 2 can reduce the possibility that a sensing section comprising drain electrode 14, source electrode 15 and channel 16 can be deteriorated by scattering of the sample solution including the detection target substance.

In Embodiments 1 and 2, cases have been described in which channel 16 is formed of poly-silicon, but channel 16 may also be formed of amorphous silicon. In this case, also, silicon oxide film 12b, drain electrode 14, source electrode 15 and channel 16 can be formed with the same kind of semiconductor manufacturing process as used for TFT manufacture.

In Embodiments 1 and 2, sensors have been described in which a reaction field is located at a different position on silicon oxide film from a position of a channel. Therefore, with sensors according to Embodiments 1 and 2, there are few restrictions on the shape of the channel and on the area and the position of the reaction field, and also high measurement sensitivity and a high degree of freedom of layout can be achieved.

In order to improve detection precision of a biosensor, it is important that an area over which a sample solution containing a detection target substance spreads is defined. When this area can be defined, an area in which a biomolecule reacts is defined, as a result, an area through which a potential applied to the substrate is fixed. In this way, a calibration curve for concentration of the detection target substance can be stabilized, and biosensing precision can be improved. Also, since biosensors with a variety of reaction field areas can be manufactured, a biosensor having a reaction field area suitable for an intended sensing can be produced.

In Embodiments 3 to 5, manufacturing methods are described for sensors that enable the area over which a sample solution spreads on a reaction field to be defined. Also, sensor manufacturing methods are described that enable the area of a reaction field to be adjusted comparatively freely and easily.

Embodiment 3

Sensor Configuration

Figure 7:
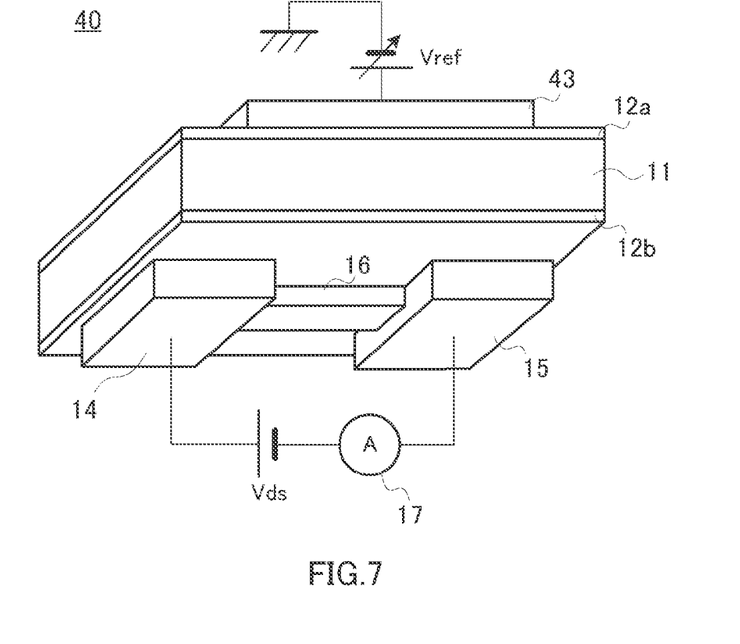
FIG. 7 is a perspective view schematically showing the configuration of a sensor according to Embodiment 3 of the present invention.
Figure 8:
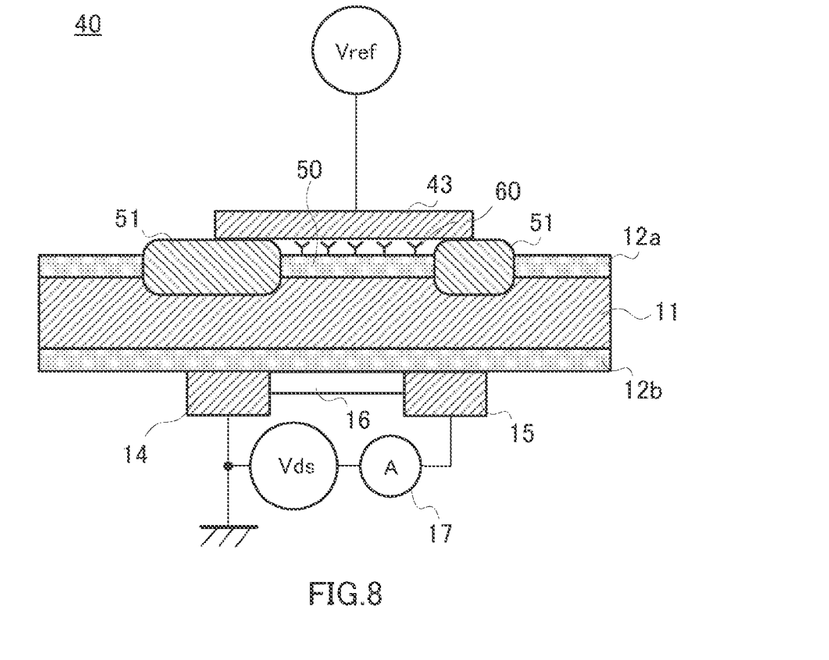
FIG. 8 is a cross-sectional view schematically showing the configuration of a sensor according to above Embodiment 3.

FIG. 7 is a perspective view schematically showing the configuration of a sensor according to Embodiment 3 of the present invention. FIG. 8 is a cross-sectional view schematically showing the configuration of the sensor. Configuration parts identical to those in FIG. 2 are assigned the same reference codes as in FIG. 2, and duplicate descriptions thereof are omitted below.

As shown in FIG. 7 and FIG. 8, sensor 40 has silicon oxide films 12a and 12b as insulating films formed on both surfaces of silicon substrate 11.

Gate electrode 43 is arranged on the opposite surface of the substrate with respect to a surface on which silicon oxide film 12a is formed. Reference voltage Vref is applied to gate electrode 43. Gate electrode 43, silicon oxide film 12a and silicon substrate 11 configure a metal-insulator-semiconductor (MIS) structure. Therefore, a gate voltage is not applied directly to silicon substrate 11. The material of gate electrode 43 is not particularly limited, as long as it is electrically conductive, and may be a metal such as gold, platinum, titanium and aluminum, or a conductive resin.

On the other hand, drain electrode 14 and source electrode 15 are formed on the surface of silicon oxide film 12b. Drain electrode 14 and source electrode 15 are electrically connected each other via channel 16 on silicon oxide film 12b. Channel 16 is formed of poly-silicon or carbon nanotubes, for example. Drain electrode 14 and source electrode 15 are connected each other via external wiring including power supply Vds and ammeter 17. By this means, a predetermined voltage is applied between drain electrode 14 and source electrode 15 by power supply Vds, and a current that flows in channel 16 is measured with ammeter 17.

The distance between drain electrode 14 and source electrode 15 is not particularly limited, but is normally on the order of 0.5 to 10 μm. This distance may be reduced in order to facilitate connection of the each electrode via channel 16. The shape and size of the source electrode and drain electrode are not particularly limited, and can be set as appropriate for a particular purpose.

Here, as shown in FIG. 8, reaction field (gate oxide film) 50 and barrier section 51 surrounding reaction field 50 are arranged on silicon oxide film 12a which is opposite to silicon oxide film 12b on which gate electrode 43 is arranged. Reaction field 50 has a function of immobilizing molecule 60 for recognizing a detection target substance. In the case of this embodiment, reaction field 50 and barrier section 51 are both formed of silicon oxide.

Examples of the molecule for recognizing the detection target substance include an antibody, enzyme, lectin, suchlike protein, nucleic acid, oligosaccharide and polysaccharide, and a substance having structure thereof. When a sensor of the present invention is used as a pH sensor or the like, it is not necessary to immobilize the molecule for recognizing the detection target substance.

The thickness of reaction field 50 is assumed to be 200 [nm] or less, and actually should preferably be on the order of 1 to 200 nm (for example, 100 nm). The thickness of barrier section 51 is assumed to be greater than that of reaction field 50, and several 1000 [nm] or less, and actually should preferably be on the order of 200 to 1000 nm (for example, 600 nm). Furthermore, it is preferable that the difference in level between the upper surface of reaction field 50 and the upper surface of barrier section 51 is on the order of 200 to 800 nm (for example, 500 nm). In actuality, the area of reaction field 50 is on the order of 25 mm$^2$.

It is preferable that barrier section 51 completely surround reaction field 50, but not necessarily completely surround. The essential point is that barrier section 51 should surround reaction field 50 to an extent that effluence of a sample solution to be provided from reaction field 50 can be prevented.

Thus, with sensor 40 of this embodiment, barrier section 51 surrounding reaction field 50 enables a detection target substance and a molecule for recognizing the detection target substance to be defined within reaction field 50 as well as to be prevented from spreading beyond reaction field 50. That is to say, the area over which a sample solution spreads to be provided on reaction field 50 can be defined.

[Biosensor Manufacturing Method]

The manufacturing method of sensor 40 configured as described above is explained below. FIG. 9 shows the manufacturing process of sensor 40. A particular feature of the manufacturing method of a biosensor according to this embodiment is that barrier section 51 is formed with local oxidation of silicon (LOCOS) process. And therefore the following description focuses on this process.

Figure 9A:
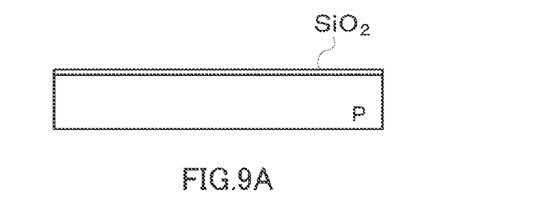
FIG. 9 shows the semiconductor manufacturing process of a sensor according to above Embodiment 3.

First, a silicon oxide ($SiO_2$) film is formed on a p-type silicon substrate by means of thermal oxidization, as shown in FIG. 9A.

Figure 9B:
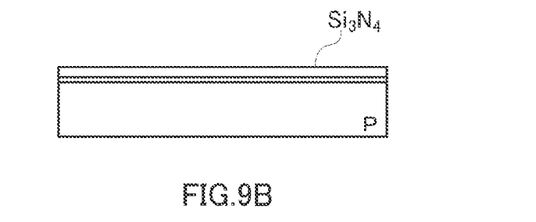

Next, a silicon nitride ($Si_3N_4$) film is deposited on the silicon oxide film by means of chemical vapor deposition (CVD) process, as shown in FIG. 9B.

Figure 9C:
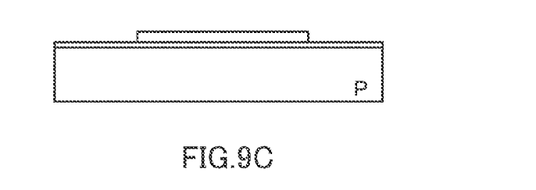

Next, the $Si_3N_4$ film is then removed by means of lithographic and etching process, as shown in FIG. 9C. The part where the $Si_3N_4$ film is removed is a part where barrier section 51 will be formed. A part where $Si_3N_4$ film remains is a part where reaction field 50 will be formed.

Figure 9D:
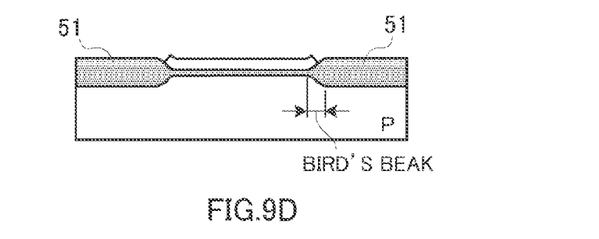

Next, oxidation processing is performed under a wet $O_2$ atmosphere at a temperature on the order of 1000° C., as shown in FIG. 9D. As $Si_3N_4$ is not oxidized, only part of silicon 11 where $Si_3N_4$ has been removed is selectively oxidized. At this process, the thickly formed silicon oxide film burrows under the $Si_3N_4$ film (forming a so-called bird's beak). In this way, barrier section 51 is formed.

Figure 9E:
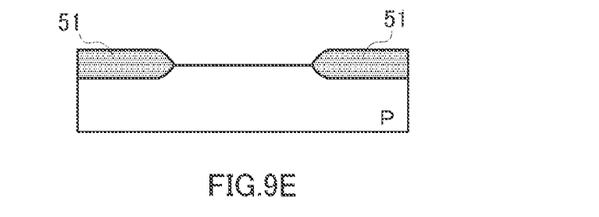
Figure 9F:
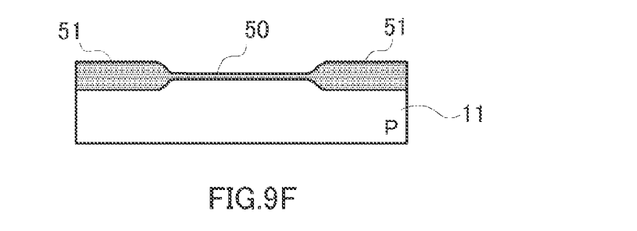

$Si_3N_4$ film is next removed as shown in FIG. 9E. And then, a gate oxide film as reaction field 50 is formed by means of thermal oxidization or vapor phase epitaxy, as shown in FIG. 9F.

Next, the silicon substrate is inverted. And on the opposite surface to the surface on which barrier section 51 and reaction field 50 have been arranged, forming a source electrode and a drain electrode, and a channel; covering the channel with an inter-layer film; forming external wiring between the source electrode and the drain electrode; and forming a surface protective film are carried out appropriately. Finally, molecule 60 for recognizing a detection target substance is immobilized on reaction field 50.

Thus, according to a biosensor manufacturing method of this embodiment, reaction field 50 and barrier section 51 surrounding the reaction field 50 are formed easily and with high precision with LOCOS process, which is conventionally method used for an element isolation. Moreover, LOCOS can also be used for element isolation of the drain region and the source region. In such a case, forming drain electrode 14 and source electrode 15, and forming barrier section 51 and reaction field 50, can be carried out in the one LOCOS process. That can simplify the manufacturing process as well as the manufacturing apparatus for the sensor. However, with regard to element isolation of the drain region and source region, it is not necessarily required for LOCOS process. The essential point is that the drain region and the source region should be arranged on a semiconductor substrate other than in the region where reaction field 50 and barrier section 51 are formed.

Embodiment 4

In Embodiment 3, a case was described in which gate electrode 43 was arranged at a position on the opposite surface to the surface on which reaction field 50 is located. A position of gate electrode 43 is not limited to the position shown in FIG. 8. In Embodiment 4, a case is described in which gate electrode 43 is attached in a fixed manner to the barrier section 51.

Figure 10:
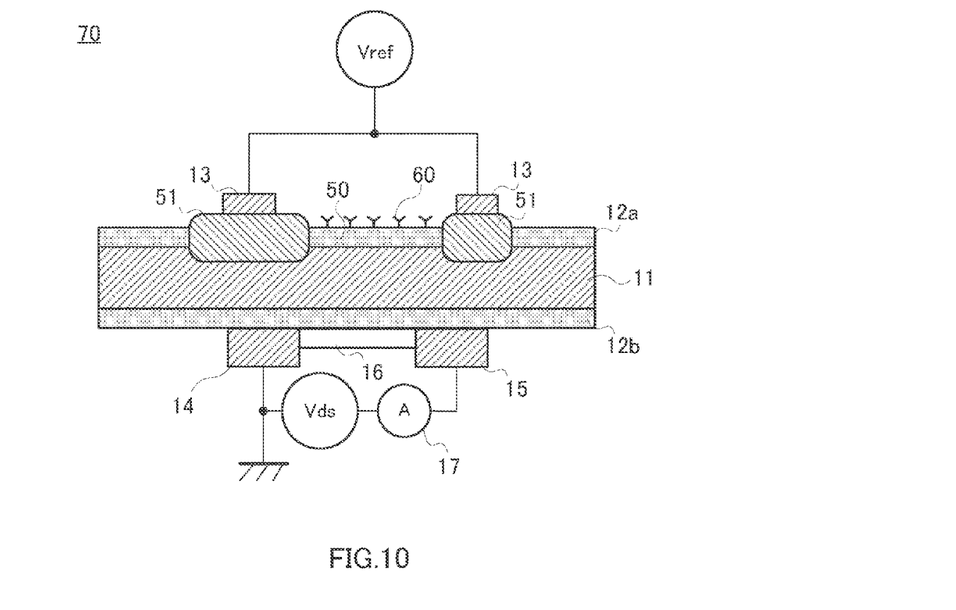
FIG. 10 is a cross-sectional view schematically showing the configuration of a sensor according to Embodiment 4 of the present invention.

FIG. 10 is a cross-sectional view schematically showing the configuration of a sensor according to Embodiment 4 of the present invention. Configuration parts identical to those in FIG. 8 are assigned the same reference codes as in FIG. 8, and duplicate descriptions thereof are omitted below.

As shown in FIG. 10, gate electrode 43 is attached in a fixed manner to the surface of barrier section 51 of sensor 70. That is to say, in sensor 70, gate electrode 43 is arranged at a different position from a position facing to field 50 (as shown in FIG. 8), and is attached in a fixed manner to the barrier section 51. For example, when both of the barrier section 51 and the gate electrode 43 have the shape of square frame surrounding reaction field 50, and the gate electrode 43 is placed in contact with the upper surface of barrier section 51, an electric field passing through reaction field 50 can be strengthened.

Also, as compared with a case in which gate electrode 43 is provided at a position shown in FIG. 8, the configuration of Embodiment 4 can effectively prevent electrification caused by contact between gate electrode 43 and barrier section 51 or a sample solution to be provided.

Embodiment 5

In Embodiments 3 and 4, a so-called back-gate type sensor 40 is described. In back-gate type sensor 40, drain electrode 14 and source electrode 15 are formed on the opposite surface with respect to the surface on which reaction field 50 and barrier section 51 are arranged.

Figure 11:
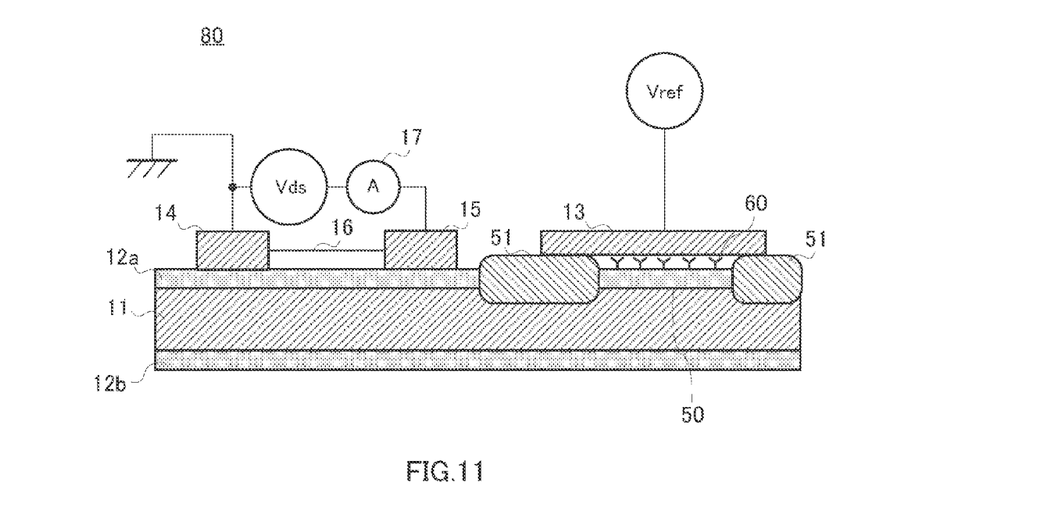
FIG. 11 is a cross-sectional view schematically showing the configuration of a sensor according to Embodiment 5 of the present invention.

In Embodiment 5, a so-called side-gate type biosensor are described. FIG. 11 is a cross-sectional view schematically showing the configuration of a sensor according to Embodiment 5 of the present invention. Configuration parts identical to those in FIG. 10 are assigned the same reference codes as in FIG. 10, and duplicate descriptions thereof are omitted below.

As shown in FIG. 11, in sensor 80, drain electrode 14 and source electrode 15 are arranged on the surface of the silicon substrate on which reaction field 50 and barrier section 51 are arranged.

According to this embodiment, the same kind of effects can be obtained as with the back-gate type sensors of Embodiment 3 and 4—that is, barrier section 51 surrounding reaction field 50 enables a detection target substance and a molecule for recognizing detection target substance provided on reaction field 50 to be defined by barrier section 51, as well as to be prevented from spreading beyond the area of reaction field 50. And also barrier section 51 can define the area over which a sample solution to be provided on reaction field 50 spreads.

Embodiment 6

In Embodiments 3 to 5, cases are described in which barrier section 51 is formed with LOCOS process and reaction field 50 was formed using vapor phase epitaxy. In Embodiment 6, a sensor manufacturing method is described whereby barrier section 51 and reaction field 50 are formed by means of photolithography process. FIG. 12 shows a sensor manufacturing process using semiconductor fabrication according to Embodiment 6 of the present invention.

Figure 12A:
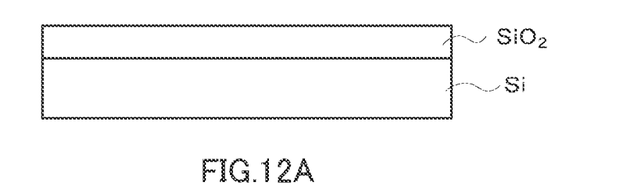
FIG. 12 shows the semiconductor manufacturing process of a sensor according to Embodiment 6 of the present invention.

First, a silicon oxide film is formed on a silicon substrate by means of thermal oxidization, as shown in FIG. 12A. Here, the thickness of the formed silicon oxide film is adjusted to a value obtained by subtracting the thickness of reaction field 50 from the thickness of barrier section 51.

Figure 12B:
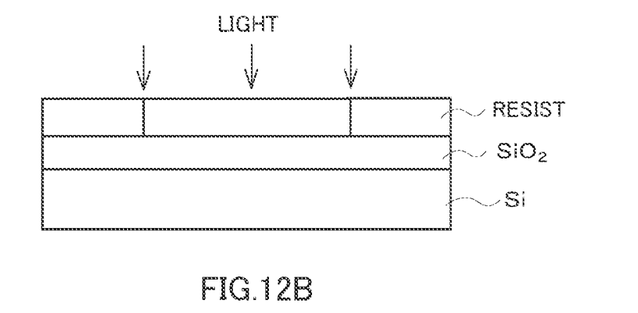

Next, the entire silicon oxide film is coated with a resist, and then an area corresponding to reaction field 50 is irradiated with light, as shown in FIG. 12B.

Figure 12C:
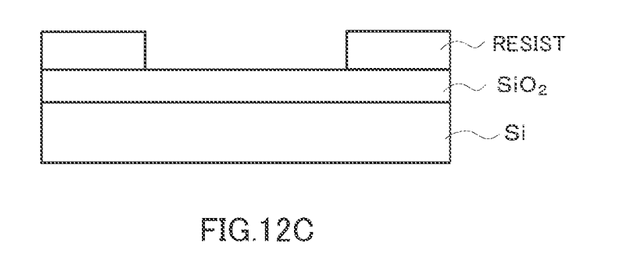

The irradiated resist is then removed by means of development processing, as shown in FIG. 12C.

Figure 12D:
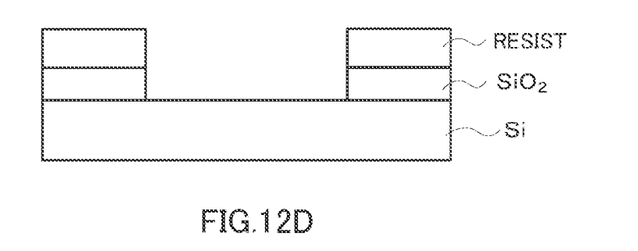

Next, the exposed part of silicon oxide film, from which the resist has been removed, is subject to etching with hydrofluoric acid, as shown in FIG. 12D.

Figure 12E:
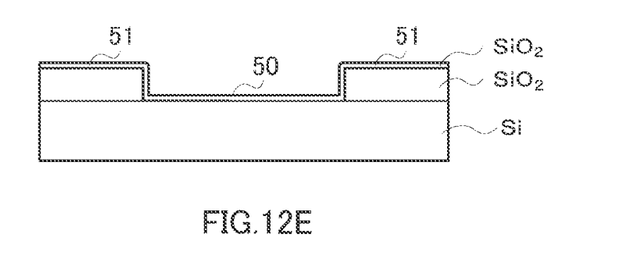

After the etching, a silicon oxide film having the appropriate thickness for reaction field 50 is formed by means of thermal oxidization or vapor phase epitaxy, as shown in FIG. 12E. By this means, both of reaction field 50 and barrier section 51 which has a thicker silicon oxide film than reaction field 50 can be formed.

The above description presents examples of preferred embodiments of the present invention, but the scope of the present invention is not limited to these. For example, in the above embodiments, cases have been described in which the present invention is applied to a biosensor manufacturing method, but the present invention is not limited to this, and is applicable to a wide range of manufacturing methods for sensors including an FET. When the present invention is applied to a manufacturing method for a sensor including an FET other than a biosensor, the above-described step of immobilizing a molecule for recognizing a detection target substance on the reaction field can be omitted.

In the above embodiments, the terms "sensor" and "sensor manufacturing method" have been used, but this is simply for convenience of description. The terms "sensor" can also means "biosensor" or the like. Also, the type, number, processing method, and so forth of the detection target substances and the molecules for recognizing detection target substance, which are referred to in the above-described sensors and sensor manufacturing methods, are not limited to those in the above embodiments.

The disclosure of Japanese Patent Application No. 2008-139045, filed on May 28, 2008, including the specification, drawings and abstract, is incorporated herein by reference in its entirety.

INDUSTRIAL APPLICABILITY

A sensor and sensor manufacturing method according to the present invention is applicable to a wide range of manufacturing methods for sensors that include an FET.

REFERENCE SIGNS LIST

10, 30, 40, 70, 80 Sensor
11 Silicon substrate
12a, 12b Silicon oxide film
13, 43 Gate electrode
14 Drain electrode
15 Source electrode
16 Channel
20, 50 Reaction field
51 Barrier section
21, 60 Molecule for recognizing detection target substance

The invention claimed is:

1. A sensor comprising:
a silicon substrate having a silicon oxide film;
a source electrode and a drain electrode, the source electrode and the drain electrode being arranged on the silicon oxide film;
a channel being arranged on the silicon oxide film and being electrically connected to the source electrode and drain electrode;
a reaction field having a thickness and being located on the silicon oxide film;
a barrier section surrounding the reaction field and being thicker than the reaction field, the barrier section formed of an insulating material; and
a gate electrode being arranged on the barrier section;
wherein the source electrode and the drain electrode are arranged on a different place from the reaction field.

2. The sensor according to claim 1, wherein the reaction field is surrounded by the gate electrode.

3. The sensor according to claim 1, wherein the barrier section is formed of silicon oxide.

4. The sensor according to claim 1, wherein the channel is a poly-silicon film or amorphous silicon film.

5. The sensor according to claim 1, wherein:
the silicon substrate has the silicon oxide film on either or both surfaces; and
the reaction field, the source electrode, the drain electrode and the channel are arranged on the same silicon oxide film.

6. A method for manufacturing a sensor that includes a field effect transistor having a semiconductor substrate, a silicon oxide film formed on a surface of the semiconductor substrate, and an electrode connected to the silicon oxide film, part of the silicon oxide film being a reaction field for a detection target substance, the method comprising:
forming a silicon oxide film on a silicon substrate;
forming a channel on the silicon oxide film;
forming a source electrode and a drain electrode on the channel;
forming a reaction field having a thickness on the silicon oxide film;
forming a barrier section formed of an insulating material on the silicon oxide film, the barrier section surrounding the reaction field and being thicker than the reaction field; and
forming a gate electrode on the barrier section,
wherein the source electrode and the drain electrode are arranged on a different place from the reaction field.

7. The method according to claim 6, wherein the drain electrode and the source electrode are formed on the surface of the silicon substrate on which the reaction field and the barrier section are formed.

8. The method according to claim 6, wherein the gate electrode is formed so as to surround the reaction field.

9. The method according to claim 6, wherein the barrier section is formed of silicon oxide.

* * * * *